(12) United States Patent
Ram et al.

(10) Patent No.: US 8,275,631 B2
(45) Date of Patent: Sep. 25, 2012

(54) EXECUTING CLINICAL PRACTICE GUIDELINES

(75) Inventors: Prabhu Ram, Bellevue, WA (US); David R. Berg, Bellingham, WA (US); John M. Thrun, Renton, WA (US); Bing Wu, Seattle, WA (US); Chandresh Taunk, Bellevue, WA (US); Robert M. Abarbanel, Bainbridge Island, WA (US); James Guy Mansfield, Bothell, WA (US)

(73) Assignee: IDX Systems Corporation, Burlington, VT (US)

( * ) Notice: Subject to any disclaimer, the term of this patent is extended or adjusted under 35 U.S.C. 154(b) by 1626 days.

(21) Appl. No.: 10/942,285

(22) Filed: Sep. 15, 2004

(65) Prior Publication Data

US 2005/0108049 A1    May 19, 2005

Related U.S. Application Data

(60) Provisional application No. 60/503,278, filed on Sep. 15, 2003.

(51) Int. Cl.
    *G06Q 10/00* (2006.01)
(52) U.S. Cl. ............................................... 705/2; 705/3
(58) Field of Classification Search .................... 705/2, 3
    See application file for complete search history.

(56) References Cited

U.S. PATENT DOCUMENTS

| | | | |
|---|---|---|---|
| 5,924,074 A | 7/1999 | Evans | |
| 6,139,494 A | 10/2000 | Cairnes | |
| 6,188,988 B1 * | 2/2001 | Barry et al. | 705/3 |
| 6,505,196 B2 * | 1/2003 | Drucker et al. | 707/751 |
| 6,804,656 B1 | 10/2004 | Rosenfeld et al. | |
| 2002/0010597 A1 | 1/2002 | Mayer et al. | |
| 2003/0110059 A1 | 6/2003 | Janas, III et al. | |
| 2003/0125983 A1 * | 7/2003 | Flack et al. | 705/2 |
| 2004/0073453 A1 | 4/2004 | Nenov et al. | |
| 2004/0261063 A1 * | 12/2004 | Wang et al. | 717/136 |
| 2005/0065818 A1 | 3/2005 | Brinkman et al. | |
| 2005/0234740 A1 * | 10/2005 | Krishnan et al. | 705/2 |

FOREIGN PATENT DOCUMENTS

WO        02/37337        5/2002

(Continued)

OTHER PUBLICATIONS

International Search Report and Written Opinion, PCT/USO4/30208, Feb. 9, 2006, 7 pages.

(Continued)

*Primary Examiner* — Robert Morgan
*Assistant Examiner* — Maroun Kanaan
(74) *Attorney, Agent, or Firm* — Andrus, Sceales, Starke & Sawall, LLP (57) ABSTRACT

A clinical practice guideline can be implemented using a guideline execution engine. The engine can interpret the clinical practice guideline, obtain medical data stored in a clinical information system (CIS), and implement an action in response to execution of the clinical practice guideline based on medical data for a patient obtained from the CIS. The use of the CIS medical data in guideline execution beneficially allows the guideline to be tightly integrated into the real-time workflow of a clinician in a clinical setting and to provide patient-specific guideline recommendations. A VMR/actions interface facilitates communications between a guideline execution system and a CIS by processing a request for medical data from the guideline execution engine and implementing actions on the CIS requested by the guideline execution engine.

7 Claims, 5 Drawing Sheets

FOREIGN PATENT DOCUMENTS

| | | |
|---|---|---|
| WO | 02/37337 A2 | 5/2002 |
| WO | 03/040990 | 5/2003 |
| WO | 03/040990 A2 | 5/2003 |

OTHER PUBLICATIONS

International Search Report dated Feb. 9, 2006.
Quaglini et al. "Guideline-based careflow systems", Artificial Intelligence in Medicine, Elsevier, vol. 20, No. 1, Aug. 2000, pp. 5-22.
Dazzi et al., "A Patient Workflow Management System Built on Guidelines", Symposium, American Medical Informatics Association, 1997, pp. 146-150.
Ciccarese et al., A Guideline Management System: Medinfo, Proceedings of the Conference on Medical Informatics, North-Holland Publ., Amsterdam, NL, vol. 11, No. Pt. 1.
Wang et al., "GESDOR—A Generic Execution Model for Sharing of Computer-Interpretable Clinical Practice Guidelines", AMIA Annual Symposium Proceedings/AMIA Symposium, 2003.
Beard et al., "Standards-Based Sharable Active Guideline Environment (SAGE): A Project to Develop a Universal Framework for Encoding and Disseminating Electronic Clinical Practice Guidelines", AMIA 2002 Symposium, Bio Medical Informatics: One Discipline. Annual Symposium of the American Medical Informatics Association, Proceedings American Medical Informatics Assoc., Bethesda, MD, p. 973.
Peleg et al., "Comparing Computer-interpretable Guideline Models: A Case-study Approach", Journal of the American Medical Informatics Association, Hanley and Belfus, Philadelphia, PA, vol. 10, No. 1, Jan. 2003, pp. 52-68.
Johnson et al., "A Virtual Medical Record for Guideline-Based Decision Support", Proceedings of the American Medical Informatics Association Annual Symposium, 2001, pp. 294-298.
Wang et al., "Representation of Clinical Practice Guidelines for Computer-Based Implementations", Medinfo 2001, Proceedings of the 10th World Congress on Medical Informatics IOS Press, Amsterdam, NL, vol. 1, pp. 285-289.
Wang et al., "GLEE—A Model-Driven Execution System for Computer-Based Implementation of Clinical Practice Guidelines", Proceedings of the American Medical Informatics Association Annual Symposium, 2002, pp. 855-859.
EP Search Report dated Jul. 9, 2007.
European Patent Office, Summons to Attend Oral Proceedings Pursuant to Rule 115(1) EPC mailed Dec. 18, 2010 (15 pgs).
Guideline based careflow system, S. Quaglini et al., Artificial Intelligence in Medicine, Elsevier, vol. 20, No. Aug. 2000, pp. 5-22, XP002356295, ISSN: 0933-3657.
A patient workflow management system built on guidelines, L. Dazzi et al., Symposium, American Medical Informatics Association, 1997, pp. 146-150, XP002356294.
A guideline management system, P. Ciccarese et al., Medinto, Proceedings of the Conference on Medical Informatics, North-Holland Publ., Amsterdam, NL, vol. 11, No. Pt. 1, Sep. 7, 2004, pp. 28-32, XP002356293.
GESDOR—a generic execution model for sharing of computer-interpretable clinical practice guidelines, D. Wang et al., AMIA . . . Annual Symposium Proceedings/AMIA Symposium, AMIA Symposium 2003, Nov. 8, 2003 thru Nov. 12, 2003, pp. 694-698, XP002439237, ISSN: 1559-4076.
Standards-based sharable active guideline environment (SAGE): a project to develop a universal framework for encoding and disseminating electronic clinical practice guidelines, N. Beard et al., AMIA 2002 Symposium, Bio Medical Informatics: One Discipline, Annual Symposium of the American Medical Informatics Association, Proceedings American Medical Informatics Assoc. Bethesda, MD USA 2002, p. 973, XP002439238.
Comparing computer-interpretable guideline models: a case-study approach, M. Peleg et al., Journal of the American Medical Informatics Association, Hanley and Belfus, Philadelphia, PA, US, vol. 10, No. 1, Jan. 2003, pp. 52-68, XP002356296, ISSN: 1067-5027.
A virtual medical record for guideline-based decision support, P.D. Johnson, et al., Proceedings of the American Medical Informatics Association Annual Symposium, 2001, pp. 294-298, XP009052774.
Representation of clinical practice guidelines for computer-based implementations, Wang Dongwen et al., Medinfo 2001, Proceedings of the 10th World Congress on Medical Informatics IOS Press Amsterdam, Netherlands, vol. 1, 2001, pp. 285-289, vol. 1, XP002439239, ISBN: 1-58603-194-5.
GLEE-A model-driven execution system for computer-based implementation of clinical practice guidelines, D. Wang et al., Proceedings of the American Medical Informatics Association Annual Symposium, 2002, pp. 855-859, XP002342376.

* cited by examiner

EXECUTING CLINICAL PRACTICE GUIDELINES

CROSS REFERENCE TO RELATED APPLICATIONS

This application claims the benefit of U.S. provisional application No. 60/503,278, entitled "Executing Clinical Practice Guidelines" and filed Sep. 15, 2003, which is hereby incorporated by reference in its entirety herein.

STATEMENT REGARDING FEDERALLY SPONSORED RESEARCH OR DEVELOPMENT

The U.S. Government has certain rights in this invention pursuant to Grant No. 70NANB1H3049, awarded by the U.S. National Institutes of Health and the National Institute of Standards and Technology.

BACKGROUND

1. Field of the Invention

This invention relates generally to the implementation of clinical practice guidelines, and in particular to a system for executing clinical practice guidelines based on data stored in a clinical information system.

2. Background of the Invention

The potential benefits of standardizing clinical practices in medical care have been widely recognized. By following medical (or "clinical practice") guidelines, clinicians can work more efficiently, and thus reduce unwanted variation, medical errors, and the cost of providing service. Best practices can be shared and distributed as they are developed, improving the quality of care. Guidelines, largely authored by medical associations, are generally conveyed in written form, such as through textbooks, magazines, newsletters, or PDFs. Under the existing paradigm, physicians and other clinicians are expected to read these guidelines and apply them appropriately at the point of care in a hospital or other health-care provider setting.

However great, the promise of clinical practice guidelines remains unmet because of several obstacles. Some aspects of the guidelines may be open to interpretation by clinicians and require translation to the local clinical setting. Guidelines are often poorly integrated into day-to-day workflow, with a lack of intervention modes in support of guideline recommendations. The risk of medical mistakes is especially great in high-stress situations such as emergency room treatment. The long lead times typically required to develop and deploy guidelines also mean that guidelines may quickly become outdated and frequently do not reflect the state-of-the-art in medical care.

For these reasons, there is a need to improve the delivery of clinical guidelines beyond the passive distribution of written materials to end-users by providing systems that allow clinicians to easily and effectively use clinical practice guidelines.

SUMMARY OF THE INVENTION

In an embodiment, an automated guideline execution engine is provided that can implement a clinical practice guideline based on medical data stored in a clinical information system (CIS). The engine includes a core engine for executing the clinical practice guideline and a binding module for obtaining medical data stored in the CIS responsive to execution of the clinical practice guideline and for implementing an action in response to execution of the clinical practice guideline based on medical data obtained from the CIS. Such an engine can be used to provide support in implementing a guideline for a specific patient.

In another embodiment, the binding module is configured to create a request for the medical data formatted in accordance with a web services protocol published by an interface layer for retrieving the medical data from an external source. Flexibly, this allows the engine to obtain data in a platform-neutral way and from a variety of heterogeneous CISs. It also reduces the need for duplicate versions of the same medical data to be stored both in the CIS and the engine, reducing the costs associated with maintaining multiple sets of data and the risk that outdated medical data will be used.

Also provided is a virtual medical record (VMR)/actions interface that facilitates communications between a clinical practice guideline execution engine and a CIS. The interface includes a services module for processing a request for medical data stored in the CIS from the guideline execution engine and for providing a response containing the requested medical data to the guideline execution engine, and an actions module for implementing actions on the CIS requested by the guideline execution engine. In various embodiments, the actions module can, for instance, provide a notification to the CIS, supply a recommendation to the CIS, insert a diagnosis of a problem into the patient record in the CIS or schedule an appointment in the CIS.

Embodiments of the invention support dramatic improvements in the efficiency and quality of medical care. An automated guideline execution engine can be used to automatically carry out several actions in response to, for instance, a lab result indicating that a patient has diabetes. The engine, interpreting a clinical practice guideline relevant to the patient's condition could set up goals and procedures for the patient to help the patient reduce her blood pressure to a healthy level. It could also schedule follow up exams, order prescriptions, or specify additional precautions. In addition, the engine might schedule yearly eye and foot exams to look for complications, recommend certain types of drugs, and/or send an alert to the clinician if the patient's measured blood pressure is not within an acceptable range next time it is checked. By providing the ability to automate aspects of care, embodiments of the invention reduce the burden on practitioners and the risk of medical error and/or misapplication of clinical guidelines.

The figures depict embodiments of the present invention for purposes of illustration only. One skilled in the art will readily recognize from the following description that alternative embodiments of the structures and methods illustrated herein may be employed without departing from the principles of the invention described herein.

DETAILED DESCRIPTION OF THE PREFERRED EMBODIMENTS

Guideline Execution System

Figure 1:
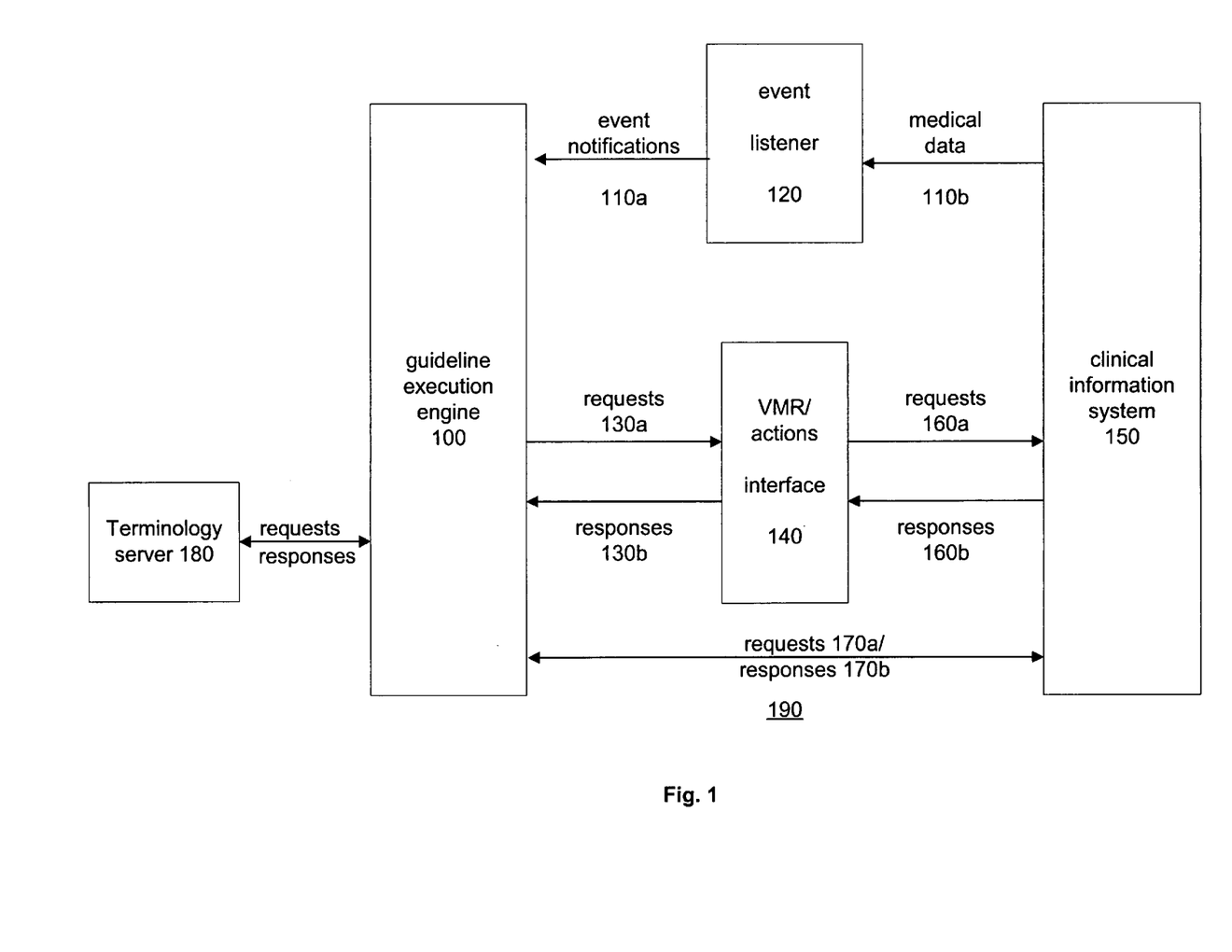
FIG. 1 is a high-level block diagram of a guideline execution system in accordance with an embodiment of the invention.

FIG. 1 is a high-level block diagram of a guideline execution system 190 in accordance with an embodiment of the invention. The system 190 includes a guideline execution engine 100, a clinical information system (CIS) 150, and a virtual medical record (VMR)/actions interface 140 that facilitates communication between the execution engine 100 and the CIS 150. The execution engine 100 executes clinical practice guidelines. During the course of guideline execution, the engine 100 makes requests 130a for information stored in the CIS 150. The VMR/actions interface 140 responds to these requests 130a by sending its own requests 160a to the CIS 150 to get the desired information and returns responses 130b to these requests to the execution engine 100. At certain points, the guideline may instruct that an action be taken to provide a patient with a course of treatment recommended by the guideline. Requests 130a to perform one or more actions in accordance with the guideline recommendation in the CIS 150 are provided automatically by the execution engine 100 to the CIS 150 through the interface 140, and responses 160b from the CIS 150 are returned accordingly. Requests 170a comprising command signals may also be sent directly to the guideline execution engine 100 from the CIS 150 to access or control aspects of the engine 100, and responses 170b may be sent back to the CIS 150. Using this system 190, guideline recommendations can be automatically translated into clinical outcomes without the need for clinical intervention.

Guideline Execution Engine

The guideline execution engine 100 executes a clinical practice guideline and implements an action responsive to execution of the guideline. As used herein, reference to the "execution, processing," "interpretation" or the like of a guideline may refer to advancing through logic contained in the guideline. This may be accomplished, among other methods, by running on a processor one or more interpreted or compiled computer programs representative of the guideline. In certain embodiments, the engine 100 reads and deploys the guideline prior to its execution. This process may comprise parsing the guideline to determine the execution paths the engine may need to follow to execute this guideline, validating the syntactic correctness of the guideline, determining triggering events based on the guideline, and/or determining where medical data called for during execution of the guideline is to be retrieved.

During the course of processing a guideline, the engine 100 may obtain various types of data as called for by the guideline. For instance, the guideline may obtain terminology data from the terminology server 180 to get a list of medical terms represented by a medical concept or resolve concepts that are compositions of other terms. In addition, the engine 100 may require various types of patient data in order to process the guideline. To gather this information, the engine 100 interfaces with the CIS 150 through a VMR/actions interface 140, which accesses the patient information stored in the CIS 150 on an as-needed basis. The engine 100 may also obtain locally stored non-patient specific data such as time interval data, or other data, in order to carry out process steps in the guideline. As the engine processes the guideline, it may also send requests to perform certain actions in accordance with the guideline. In an embodiment, these requests are sent through the VMR/actions interface 140, which in turn interacts directly with the CIS 150.

CIS

The CIS 150 is a system utilized by a hospital or other clinical care provider to track information about patients and other data utilized in the operation of the care provider. In an embodiment, the CIS 150 is the IDX Carecast™ System. Other CIS's 150 such as Cerner Corporation's Millenium™ system, Eclypsis Corporation's Sunrise™ system, and Seimens Corporation's Soarian™ system can also be used. The CIS 150 is integrated into the workflow of the care provider and supports clinical processes such as tracking orders, results, pharmacy and care documentation, as well as administrative/financial processes such as scheduling, registration, admitting, charging and billing. Supporting various operations of the care provider, the CIS 150 is regularly accessed by doctors, nurses, clinicians, administrators, and others, usually through a client computer (not shown). The client computer in the case of IDX Carecast™ typically utilizes either a standard web browser or a specialized JAVA-based client. Access to the CIS 150 is controlled through a log-on or other conventional authentication system. The CIS 150 includes a front-end module through which clients can access and store patient information and carry out various processes.

The CIS 150 stores patient information that is accessed by the guideline execution engine 100 through the interface 140. This information can be stored in a variety of formats and methods. For instance, the CIS 150 may include findings such as those made by clinicians or returned by modalities. It may also store information about known medical problems related to a patient, such as whether the patient is diabetic or suffers from certain allergies. The CIS 150 typically will also contain demographic information related to the patient including the patient's name, address, age, gender, next of kin, etc. Financial and billing data may also be stored in the CIS 150, including patient address, insurance coverage information, and relevant authorizations. The patient information may be stored in a general or specific database, flat file, or other format. The CIS 150 also contains various modules for supporting clinical functions such as scheduling tests or appointments and specifying health targets. These and other modules are discussed in more detail with reference to FIG. 3. As used herein, the term "module" can refer to computer program logic for providing specified functionality. A module can be implemented in hardware, firmware, and/or software. In addition, one of skill in the art will recognize that the concept and functionality of a module may be disclosed without specifically using the term "module."

VMR/Actions Interface

The VMR/actions interface 140 facilitates communications between the guideline execution engine 100 and the CIS 150. The engine 100 may request, for instance, the retrieval of data contained in the CIS, the storage of medical data to the CIS 150 or the performance of an administrative or other action in the CIS 150. The interface 140 broadcasts protocols dictating how such requests should be formulated. For instance, the interface 140 may advertise methods to get or set data from or perform actions for instance on the CIS that it supports, and the request in turn may be comprised of one or more of these methods. By formatting its requests in accordance with these protocols, the engine 100 can communicate its data or action requests without the need to identify the precise source data or location of the action.

Upon receiving a request from the engine 100, the interface 140 translates the request into one or more CIS 150 specific calls. For instance, the interface 140 may call the notifications portion of the CIS 150 and insert a message or reminder to a clinician concerning a patient. Or, the interface 140 may request medical data concerning a specific patient stored in a particular database in the CIS. By making medical data contained in the CIS 150 accessible to the engine 100 through the interface 140, the present system 190 avoids the need to locally store medical data and ensures that up-to-date patient data is made available to the guideline execution engine 100. The interface 140 may also supply login or password functionality to the engine 100, to ensure that the privileged required to perform a request for instance, on the CIS 150, are transported as needed. Once the request has been processed by the interface 140, a confirmation is sent back to the engine 100.

Event Listener

The system 190 includes an event listener 120 that monitors changes in clinical data and notifies the execution engine 100 when an event that has consequences for the execution of a guideline (referred to herein as a "triggering event") takes place. For example, if the engine 100 contains a diabetes guideline, and a patient with diabetes is created in the CIS 150, the event listener 120 will send a notification 110a to the engine 100 to initiate processing of the guideline 100. Later during the course of the patient's treatment, if the patient's new weight is recorded and exceeds a certain upper limit, resulting in another triggering event, the listener 120 sends a second notification 110a to the engine resulting in the execution of the appropriate branch of the guideline. The listener 120 may be implemented as a web service, allowing for broad interoperability, and can be used by any conforming system such as a CIS 150 to publish events.

Terminology Server

The guideline execution system 190 optionally also includes a terminology server 180 that stores terminology data that may be used to support execution of a guideline by the engine 100. In an embodiment, an encoded guideline is authored using standard clinical terminology hierarchies such as SNOMED CT, LOINC, or other such hierarchy. The terminology server 180 has information about the relevant hierarchy and maintains information about the relationship between terms of the hierarchy. Execution of a guideline, for example, may require a determination of whether the patient has diabetes. In order to make this determination, the engine 100 sends a request to the terminology server 180 for all of the various sub-types of diabetes. These subtypes are also known as the "subsumed terms" associated with diabetes or the set of unique medical IDs subsumed within the term "diabetes." In response to receiving the parent identifier of "diabetes," the terminology server 180 returns the set of subsumed terms. Using these subsumed terms, the engine 100 can query the CIS 150 for the full complement of possible types of diabetes to evaluate whether the condition is met. The terminology server 180 may also be called upon by the execution engine 440 to resolve term expressions, composite terms created by guideline encoders to represent certain medical concepts.

The terminology server 180 may comprise a module hosted separately from the execution engine 100. In one embodiment, the terminology server 180 comprises the Distributed Terminology Server (DTS) offered by Apelon Inc., and can be regularly updated as new terminology and other data becomes public. In another embodiment, the functions provided by the terminology server 180 can be implemented by one of the modules in the CIS 150. Any of a variety of types of standardized medical terminologies can be stored and supplied by the terminology server 180. One embodiment of the terminology server 180 supports terminologies that conform to a common standard such as SNOMED CT. Such a terminology contains unique identifiers for each medical element and hierarchical terminologies for each element. For example, a medical term such as "Type II Diabetes" may subsume many types of diabetes such as Type II diabetes with renal complications, and insulin resistant Type II diabetes. If the guideline has a criterion that asks, "Does this patient have Type II Diabetes?" the encoding would ask "Does this patient have SNOMED CT: 44054006" where SNOMED CT: 44054006 is the code for Type II Diabetes. When the terminology server 180 is queried for subsumption with "SNOMED CT: 44054006", it would respond with the relevant subsumed meanings of "Type II Diabetes". If the patient has a record of any of the subsumed types of diabetes, then the guideline execution engine 100 returns a value of True.

System Communications

As described, the terminology server 180, engine 100, interface 140, CIS 150 and event listener 120 typically exchange communications, requests and/or responses during the execution of a clinical practice guideline by the engine 100. Web service protocols (e.g., J2EE or Net), typically formatted in Web Services Design Language ("WSDL") may support communications between the components 180, 100, 140, 150, & 120 to enable the interoperability of heterogeneous components with each other. For instance, the terminology server 180 may be hosted on a different platform than the guideline execution engine 100, or a single guideline execution engine 100 may be usable with different or heterogeneous CIS 150 that have unique interfaces or run in different operating environments. In one embodiment, the engine 100 operates on a Windows NT platform whereas the CIS 150 runs in a UNIX environment. In another embodiment, the guideline engine 100 and the CIS 150 run on a HP NonStop platform using a variant of the UNIX operating system and a Guardian operating system.

While the use of web services reduces the need to code specific calls for each machine component 180, 100, 140, 150 & 120, machine or application-specific code may also be used in conjunction with web services methods. In an embodiment, the guideline execution engine 100 communicates with the VMR/actions interface 140 using generic web services calls, while the VMR/actions interface 140 communicates with the CIS 150 using calls specifically coded to the CIS 150. Each of the communications described may be implemented, in part, over a secured connection on a wireline or wireless local and/or wide area network or enterprise private or public network such as the Internet and may use any conventional networking technology, such as Ethernet, TCP/IP, or HTTP.

In the system shown in FIG. 1, the execution engine 100, terminology server 180, event listener 120, VMR/actions interface 140, and CIS 150 all comprise separate and distinct elements. However, it is not necessary for every embodiment of the invention to include all of the elements depicted. Furthermore, it is not necessary for the elements to be housed as shown; the elements can be hosted by other entities or in sub-modules of the elements may stand-alone or together. In some implementations of the system, the various elements may also appear in different configurations. For instance, the listener 120 is shown in the system 190 as a module separate from the CIS 150, in other embodiments, however, the listener 120 may be integrated into the CIS 150 or another component of the system 190. Likewise, as other elements and sub-elements are described throughout the invention, it should be understood that various embodiments of the invention may exclude elements and sub-elements described, that the elements and sub-elements may be hosted in configurations other than those shown, and that elements and sub-elements, even within an element, may be hosted in different locations or by different entities than those shown.

Computer System

Figure 2:
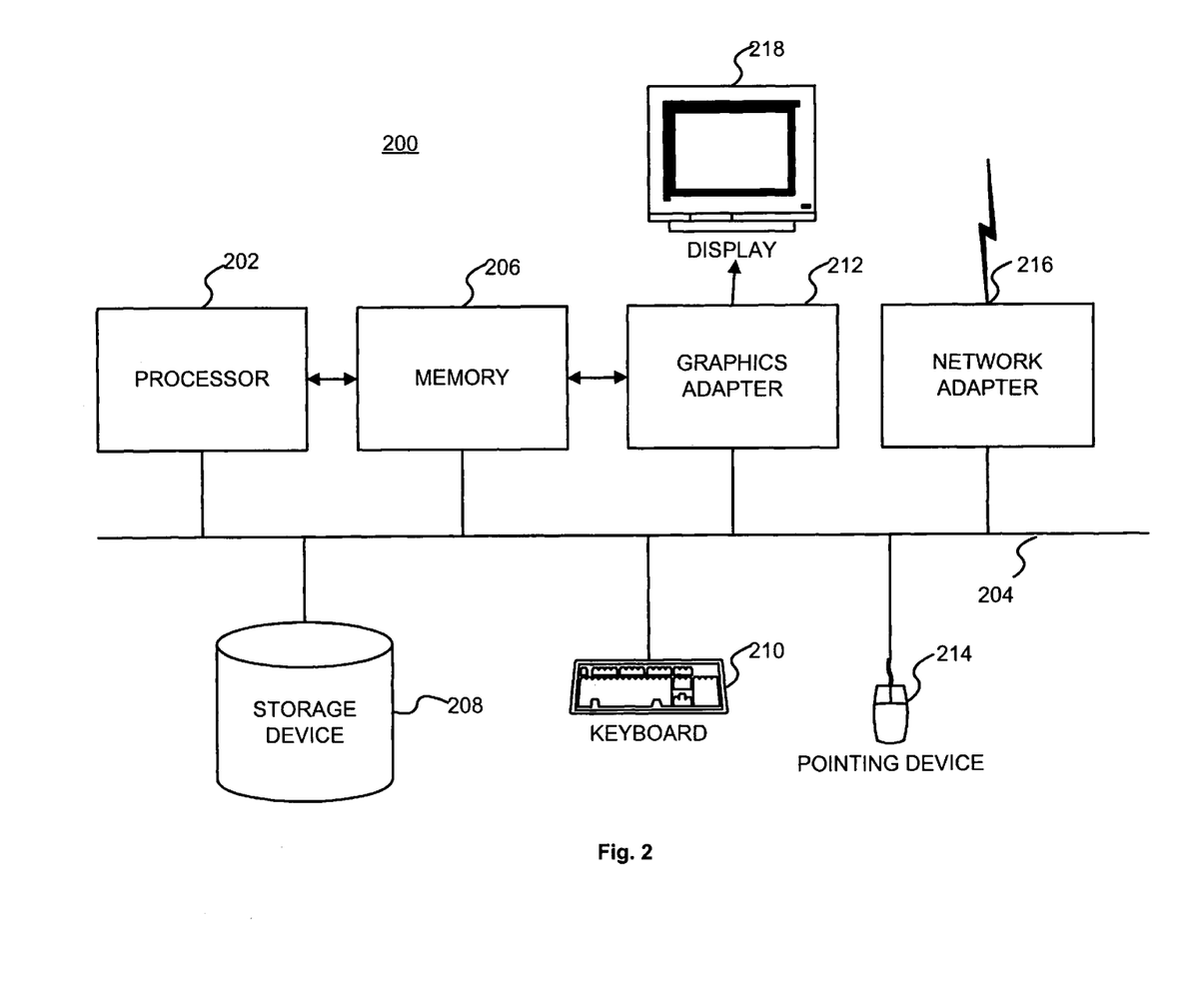
FIG. 2 is a high-level block diagram of a computer system for hosting one or more components of the system of FIG. 1 in accordance with an embodiment of the invention.

FIG. 2 is a high-level block diagram of a computer system 200 for hosting one or more components of the system of FIG. 1 in accordance with an embodiment of the invention. Other elements and sub-elements described below may also be hosted on such a computer 200. Illustrated are at least one processor 202 coupled to a bus 204. Also coupled to the bus 204 are a memory 206, a storage device 208, a keyboard 210, a graphics adapter 212, a pointing device 214, and a network adapter 216. A display 218 is coupled to the graphics adapter 212. The computer system 200 may take the form of a server, laptop, workstation, handheld device, or other general-purpose or specialized computing device.

The processor 202 may be any general-purpose processor such as an INTEL x86, SUN MICROSYSTEMS SPARC, HP NonStop, or POWERPC compatible-CPU. The storage device 208 is, in one embodiment, a hard disk drive but can also be any other device capable of storing data, such as a writeable compact disk (CD) or DVD, or a solid-state memory device. The memory 206 may be, for example, firmware, read-only memory (ROM), non-volatile random access memory (NVRAM), and/or RAM, and holds instructions and data used by the processor 202. The pointing device 214 may be a mouse, track ball, or other type of pointing device, and is used in combination with the keyboard 210 to input data into the computer system 200. The graphics adapter 212 displays images and other information on the display 218. The network adapter 216 couples the computer system 200 to the network.

The types of hardware and software within the computer system 200 may vary depending upon the implementation of the guideline execution system. For example, a guideline execution engine 100 operating in a high-volume environment may have multiple processors and hard drive subsystems in order to provide a high processing throughput, as well as be in communication with multiple CISs 150 through multiple interfaces 140. Likewise, certain embodiments may omit certain components, such as the display 218, keyboard 210, and/or network adapter 216 depending upon the specific capabilities of the system. In addition, the computer system 200 may support additional conventional functionality not described in detail herein, such as displaying images in a variety of formats, allowing users to securely log into the system, and supporting administrative capabilities.

CIS-VMR/Actions Interface

Figure 3:
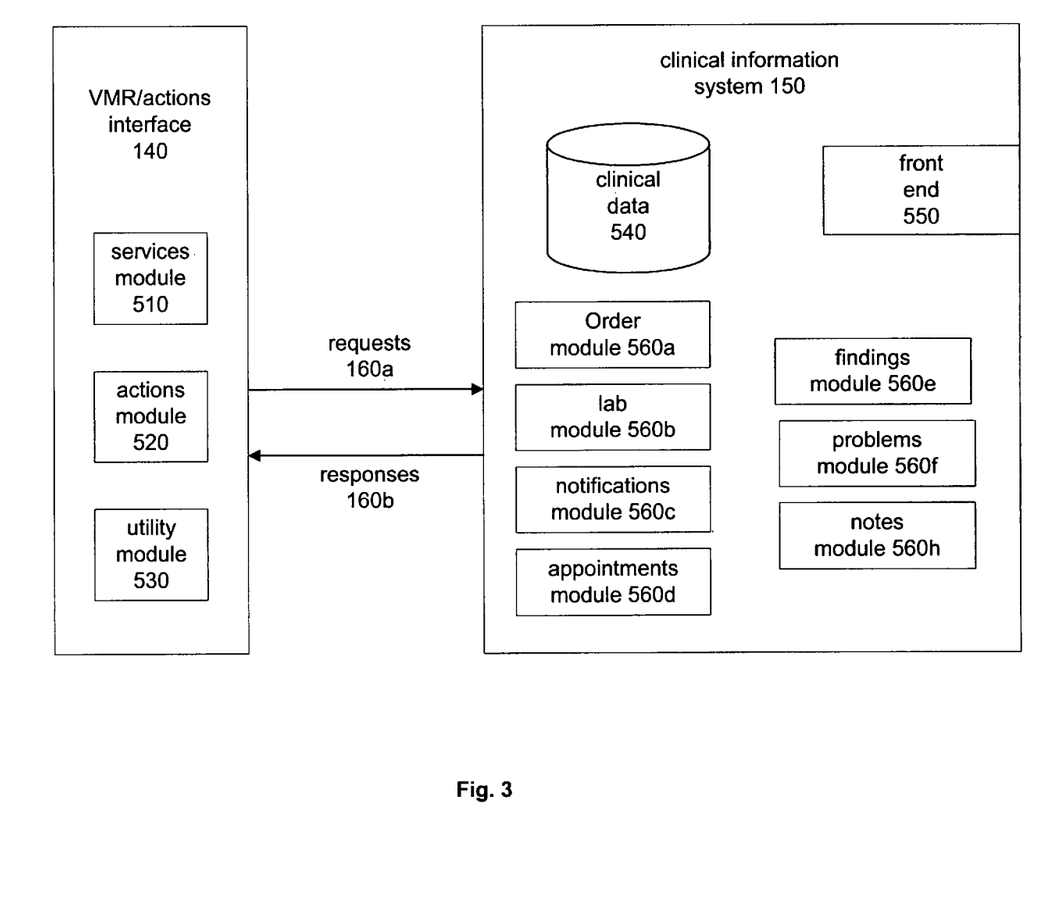
FIG. 3 depicts a virtual medical record (VMR)/actions interface in communication with a CIS in accordance with an embodiment of the invention.

FIG. 3 depicts a CIS 150 in communication with a VMR/actions interface 140 in accordance with an embodiment of the invention. The CIS 150 contains a front-end module 550, clinical data 540, and several clinical modules 560 for administering clinical care. The front-end module 550 comprises an interface through which users of the CIS 150 can access data 540, clinical modules 560, and other portions of the CIS 150 and may include a touch-screen, menu-driven, or other graphical user interface. The CIS clinical data 540 is stored in one or more repositories and comprises clinical information about patients, including for instance, physical exam data, demographic data, medical questionnaire results, medical records from previous health care providers, x-rays, and lab results. The clinical data 540 can be stored in one or more relational database management system (RDBMS), light-weight database access protocol (LDAP), flat file, or other formats.

The CIS 150 contains several clinical modules 560, including an order module 560a, lab module 560b, notifications module 560c, appointments module 560d, findings module 560e, problems module 560f, and clinical notes module 560h that are used to manage patient care. The order module 560a stores orders and order data about a patient. In general, an order is either for a lab test, for instance for blood work or an x-ray or other diagnostic test, for a prescription, or for a clinical study. The lab module 560b contains the results of lab tests and may also include administrative information regarding the tests such as the facility used by a patient or the extent of insurance coverage available for a given patient for a test. The notifications module 560c contains notifications for end-users of the CIS 150 and may function as a centralized in-box for various communications with clinicians including doctors and nurses. In an embodiment, when a doctor orders a lab test, the findings are returned to the doctor as a notification in the doctor's in-box. The appointments module 560d holds scheduling and other information related to patient visits. The findings module 560e stores observations about the patient such as the patient's temperature, height, and weight. The problems module 560f contains information pertaining to both temporary and permanent problems and problem diagnoses and allows such information to be accessed or added to a patient record. The notes module 560h is used to create/access clinical notes that have been used to annotate the patient record. Other modules such as an allergies module (not shown) for storing diagnostic, treatment, and other information about transitory and permanent allergies, or a goals module (not shown) for storing patient health goal data, may also be included.

Data in the form of appointments, notifications, diagnoses, observations, and orders may be added to the clinical modules 560 during the course of execution of a guideline. Although requests for actions originate at the engine 100, these requests are provided to the VMR/actions interface 140, which implements them on the CIS 150. An exemplary action could comprise inserting a series of tentative appointments for a patient in the appointments module 560d of the CIS 150 or sending a notification to the practitioner responsible for the patient alerting the practitioner of the appointments, for instance. Another action could comprise inserting a diagnosis of hypertension in a patient's problem list stored in the problems module 560f of the CIS 150 when the engine 100 detects that the patient's blood pressure is consistently beyond a certain threshold. As is explained in greater detail below, requests from the engine 100 to the interface 140 may be formatted using a set of generic web services methods, regardless of the format or structure of the CIS 150. Responsive to receiving the request, the interface 140 may take a CIS-specific action involving one or more of the clinical modules 560 or other portions of the CIS 150.

In an embodiment of the invention, the VMR/actions interface 140 includes three modules: a services module 510, actions module 520, and utility module 530. A services module 510 manages access by the engine 100 to medical record data stored in the CIS 150. When the engine 100 requests CIS 150 data from the interface 140, the services module 510 translates the request into an appropriate call to the CIS 140 and uses it to obtain the requested information and return it to the engine 100. The engine 100 does not need its own copy of the medical data contained within the CIS 150 but can access the medical data by making calls through the VMR/actions interface 140 to the CIS 150. The engine 100 may however cache some data locally for performance optimization reasons and employ appropriate cache management techniques to maintain the cache. Through the access it provides, the VMR/actions interface 140 supplies a "virtual medical record" (VMR) of client data to the engine 100 comprised of responses to the engine's 100 requests. Using the services module 510, the engine 100 can read any clinical (i.e., healthcare related) value from the CIS 150.

The VMR/actions interface 140 also includes an actions module 520. This module 520 performs tasks on the CIS 150 in accordance with guidelines. The actions module 520 can insert various types of data into the clinical modules 560 of the CIS 150, or may store data such as conclusions of problems (i.e., medical diagnoses), and observations/findings in other modules or the clinical data 540. The VMR/actions interface 140 may also comprise a utility module 530 that manages access to and communications with the CIS 150. For example, the utility module 530 can receive and/or store user credential, permission, login, authentication, or other access-control data provided by or associated with the guideline execution engine 100 that allow access or actions to be carried out on the CIS 150 on behalf of the engine 100. The utility module 530 can in turn create a CIS-context that specifies the access-control available to the engine 100. This context is supplied with the requests and/or actions sent by the services module 510 and actions module 520 of the interface 140 to the CIS 150.

To facilitate communication with the engine 100, the VMR/actions interface 140 makes the CIS 150 access and action methods it supports available to the engine 100. Under a web services implementation, the interface 140 publishes or broadcasts one or more sets of WSDL methods for each of the modules of the interface 140. These web services methods are formatted in Simple Object Access protocol (SOAP) (XML over HTTP/HTTPS) and advantageously are programming language independent and data format neutral and can be used by a variety of CIS 150—engine 100 combinations. The published methods comprise object-oriented function calls that can be generically used by the guideline execution engine 100 to communicate with the interface 140. The services module 510 method set may include "get" methods for retrieving information from the CIS 150 such as "get problem list( )" which returns an object having a list of diagnoses for a given patient, "get observation ( )" which returns an object containing observations about a patient, and "get allergies( )" which predictably returns an object having a list of a patient's allergies. Other methods could comprise a "problem present ( )" query as to whether a medical condition or other factor is present. The actions module 520 method set includes "set" methods by which data can be inserted, updated and stored in the CIS 150 such as "set appointment( )", which automatically schedules a series of checkups for the patient, "set goal( )", which establishes a health goal for the patient, for instance with respect to a metric such as heart rate or blood pressure, and "set notification" which delivers a notification to a clinician regarding a patient's progress.

The methods can be published or publicized by being uploaded, for instance, to a local or remote server accessible by the engine 100 through the Internet or secured private network. The guideline execution engine 100 can connect to the server to receive a list of the available interfaces or methods supported by the VMR/actions interface 140, and the organizational format (i.e., schema) of data received in response to a method call. In an embodiment, the guideline engine 100 uses this information to create method "stubs" for calling interface methods at the VMR/actions interface 140. Each "stub" comprises a generic function call handler that can be used by the guideline execution engine 100 (or other system) to access data stored in the CIS 150. By using web services methods supported by the VMR/actions interface 140, the guideline execution engine 100 can interoperate with any CIS 150 without having to customize the guideline execution engine 100 or the executing clinical practice guideline to the CIS 150. To work with a different CIS 150, only the VMR/actions interface 140, and not the engine 100, needs to be adapted to the CIS 150.

Guideline Execution Engine

Figure 4:
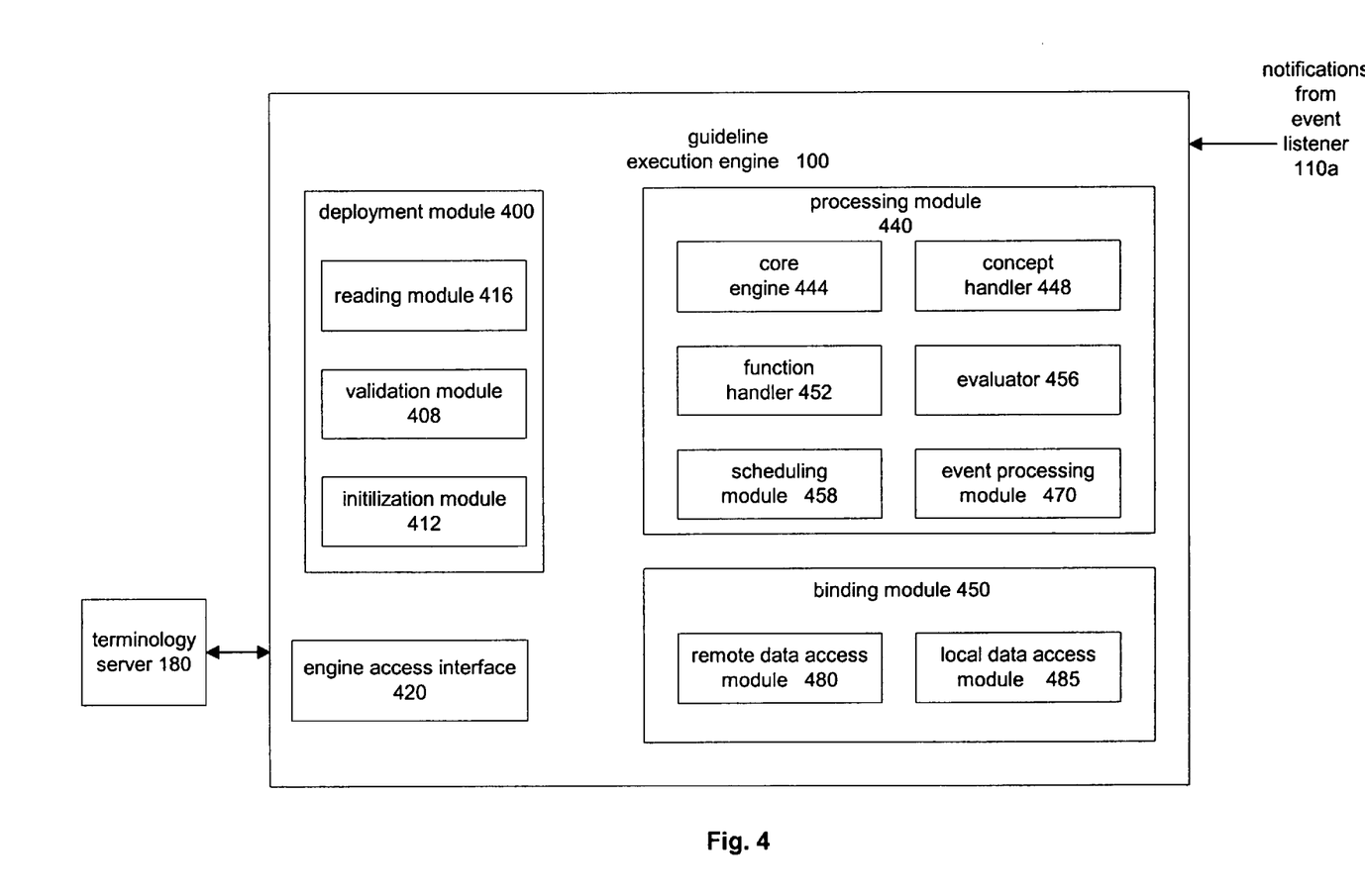
FIG. 4 is a block diagram of a guideline execution engine in accordance with an embodiment of the invention.

FIG. 4 depicts a block diagram of a guideline execution engine 100 in accordance with an embodiment of the invention. The guideline execution engine 100 contains a deployment module 400 for installing a guideline in the engine 100 to prepare it for execution, a processing module 440 for executing the guideline, and a binding module 450 for communication with internal or external systems to support execution of the guideline. The guideline execution engine 100 may be executed on a computer system 200 that hosts a J2EE server. In addition to the modules described below, the server may support Internet access and messaging functionality and host a relational database management system.

Deployment Module

The deployment module 400 receives the guideline and integrates it into the engine 100 prior to its execution. The deployment module includes a reading module 416 that reads in an encoded clinical practice guideline and produces an internal representation for execution by the engine 100, a validation module 408 for verifying the syntax of the guideline, and an initialization module 412 that determines the possible execution paths in the guideline, extracts the event triggers denoted in the guideline and sets up listeners for these events. Modules such as the reading module 416 and the validation module 408 may be packaged with graphical user interfaces to function as guideline authoring test tools. Optionally, the deployment module 400 may also include other modules (not shown) including a testing module for automated testing of guideline execution, a database module for storing non-patient guideline relevant data within the guideline execution engine 100, and an administrative module for monitoring the status of the guideline execution engine 100 and guidelines to be executed by the engine 100, and managing the performance of various modules of the engine 100.

Guideline

The reading module 416 receives a guideline and translates it into a form that is executable by the guideline execution engine 100. The guideline may be supplied to the reading module 416 in an encoded or representational form based on one or more formats including XML, Stanford University's Protégé ontology format, a JAVA object format, textual formats such RTF, or a serialized output format. The guideline may contain a number of alternative logical sequences each with a different trigger and these may be represented as different branches of a logic tree. In one embodiment, the guideline is mapped to one or more activity graphs that contain logic and various types of nodes including context nodes, decision nodes, and action nodes. In an activity graph, each segment within a guideline begins with a context node that serves as a control point in guideline execution by specifying the clinical context for that segment. If the criteria associated with a context node are satisfied, subsequent nodes in the activity graph may be executed until it reaches a node that is blocked or there are no more nodes to execute. A node in the guideline may be blocked for a particular patient for several reasons: it could be a context node waiting for a triggering event, it could be an Inquiry action waiting for a response from a clinician, it could be node that is waiting for some of its predecessor nodes to execute before this node could be executed, etc. Context nodes may specify clinical settings and resources, care-provider roles, and patient-related criteria.

A decision node in an activity graph can represent clinical decision logic by listing alternatives (typically subsequent action nodes), and specifying the criteria that need to be met to reach those nodes. During execution of an activity graph, the execution engine 100 may process all alternatives for which criteria are met, thereby allowing concurrent execution of multiple paths. Decision nodes may include specialized criteria such as comparison criteria, typically used to compare medical data returned to the engine 100 against a predetermined value or variable (e.g., patient age>18 years), presence criteria (e.g., absence of an allergy to pencillin in a patient record) that are based the presence or absence of specific data in the patient record, boolean criteria (e.g., is it true that patient is male), or goal criteria to allow goal testing (e.g., patient LDL cholesterol value is within the goal range of 120-150 mg/dl).

An action node encapsulates a set of work items that must be performed by either a computer system or a person and may conform to a format specified in the HL7 Reference Information Model Act. Actions implemented by the execution engine 100 may be synchronous or asynchronous in their interaction with the CIS. In addition, action nodes may specify preconditions that must be met before they are executed. For example, an action node may be a directive to the clinician (pediatric nurse) to obtain consent for immunization from the patient's guardian. Before the consent is supplied, the node is considered "blocked" because the condition has not been fulfilled. When the consent is provided, the engine 100 detects this triggering event and processing of the guideline continues. A specialized action node may include a "subguideline." Sub-guidelines are reusable, self-contained statements of guideline logic—analogous to sub-routines in a computer programming language. An activity graph can also call a secondary list of steps, called a decision map. The encoded guideline, in activity graph or other representational form, may be edited, revised, or otherwise "localized" to conform to local organizational and clinical policies. Assuming it has not yet been provided to the engine 100, the localized encoded guideline can then be delivered, on a CD or other medium that can be loaded onto or read by the engine 100.

Reading Module

The reading module 416 translates the encoded guideline into a representation that can be logically interpreted by the execution engine 100. The module reads the guideline from the guideline repository (or CD), extracts the execution paths that can be taken by the execution engine 100 during guideline execution. The guideline is converted to an internal canonical form and this canonical form is used during guideline execution. In an embodiment, the reading module 416 can read or can be adapted to read guidelines in several types of representational formats (e.g., XML, Protégé ontology format, etc.). If a new guideline format or encoding is introduced, the reading module 416 can be updated to allow it to work with guidelines in the new form. The reading module 416 may extract triggering events and register them with the event processing module 470. The event processing module 470 determines when a guideline should be interpreted based on these notifications. When the guideline is activated in the engine, the event processing module 470 listens for the registered triggering events. In addition, the reading module 416 may extract context points in the guideline that indicate entry points where processing may begin when the guideline is executed. Furthermore, the reading module 416 can extract guideline enrollment criteria (e.g., a patient must have diabetes in their problem list to be enrolled in the diabetes management guideline) and make the enrollment criteria available for evaluation when a guideline enrollment event occurs. Guideline enrollment and unenrollment may also be performed using an engine access interface 420. The access interface 420 provides a web services layer through which external applications such as a CIS or other application can call the guideline execution engine 100. Using the access module, the external applications can access information available to the CIS, stored locally or accessible through its interaction with the VMR/actions interface or other source, and take actions in the engine 100 including enrolling or de-enrolling a patient.

Validation Module

The other modules of the deployment module 400 perform additional processing of the guideline. The validation module 408 takes the encoded guideline and checks it for syntactical correctness. This module 408 may comprise a parser that extracts various node content from the guideline and checks to ensure that it can be recognized and read. The validation module 408 may also report missing data in guideline structures or authoring flaws for correction. Once all the checks have been performed, and errors corrected, the guideline is considered "well-formed" and in an executable form.

Initialization Module

The initialization module 412 initializes the guideline. It activates the event processing module 470 to listen for triggering events according to the guideline. In addition, through the binding module 450, the initialization module 412 also establishes access points that will be used by the engine 100 to retrieve data from the CIS 150 and to put data into the CIS 150 during the execution of a guideline. For example, the engine 100 could get data from the CIS 150 using web services methods provided by the interface 140. However, if the guideline requires data not expressed or contained in the CIS 150, the engine 100 may get the data from a local memory, storage, or other source. The initialization module includes run-time control structures that allow classes of CIS functionality through the VMR/actions interface 140 to be exposed to the guideline execution engine 100. These controls may be managed through an administrative module. The initialization module 412 is also capable of publishing a "server ready" message to the processing module 440, signaling that the guideline is ready for execution indicating that all the context entry points are ready for processing and the relevant triggering events are being listened for. Prior to completion of guideline initialization, the testing module can be used to test execution of the guideline using test data or a simulated interaction with the CIS.

Engine Access Interface

As described above, the guideline execution engine 100 also includes an engine access interface 420 that provides external systems such as the CIS 150 with access to the functions of the guideline engine 100. In one example, the CIS uses the engine access interface 420 to enroll a patient with a guideline or un-enroll the patient from the guideline. In another example, the CIS 150 may include applications that interact with the engine access interface 420 to present a question to a clinician to be answered before the guideline can continue to execute for a particular patient. In an embodiment, the engine access interface 420 is implemented with web services to promote interoperability with a variety of different accessing systems and/or applications. A command signal to manage or control engine 100 performance or guideline execution or to request data available to the engine 100 can be received, and a confirmation or response sent, through the interface 420.

Binding Module

The binding module 450 (or "binding layer") is used to bind the guideline execution engine 100 to an external system such as the CIS 150, thereby allowing the engine 100 to access, save data to, and/or perform actions on the CIS 150. Additionally, the binding module 450 may also bind data that may be stored locally and/or used for testing. During initialization of a guideline, the binding module 450 determines where and how to retrieve information required during execution of the guideline and to perform actions in accordance with guideline execution or performance. The binding module 450 associates the guideline constructs with the relevant interface 140 and other methods associated with guideline execution. The binding module 450 includes two sub-modules, the remote data access module 480 and the local data access module 485. In one embodiment, the remote data access module 480 interacts with stubs associated with the VMR/actions interface 140 and binds each VMR access method and each action method with a corresponding method in the VMR/actions interface 140 stub. The local data access module 485 can be used to provide clinical functionality that may be missing in the CIS 150 or to override certain clinical functionality that is present in the CIS 150. In another embodiment, the local data access module 485 contains structured data in XML format that may be used to provide test data to the guideline execution engine 100. For data stored in the CIS 150, the remote data access module 480 may use "get" or other methods published by the VMR/actions interface 140 to formulate its requests to the interface 140. When the data is returned, the remote data access module 480 forwards it to the core engine 444 for additional processing. When the core engine 444 executes an action node or is otherwise called on by the guideline to perform an action in execution of the guideline, the binding layer 450 through the remote data access module 480 carries out the recommended action.

To carry out an action on the CIS 150, the remote data access module 480 sends a request to perform the action to the interface 140. Requests to perform actions such as specifying a goal or sending a notification to modules in the CIS may be formatted in accordance with web service protocols provided by the interface 140. The status of requests and other aspects of guideline execution can be monitored using the administrative module. Such a module may monitor the health of the execution engine 100 and allow users to implement and oversee guideline testing, perform manual overrides, reset the engine, and perform other functions associated with guideline deployment and execution. One or more of these functions may be provided to the user through a graphical user interface or other visual monitor.

Processing Module
Core Engine

The processing module 440 performs and supports execution of a well-formed guideline that has been installed by the deployment module 400. Instances of the guideline may be executed for each patient that is enrolled in the guideline. The core engine 444 may be implemented in hardware including a dedicated processor, software, or a combination of hardware and software. The core engine 444 implements the logic contained in and flow structures associated with the guideline. Guideline execution for a particular patient may be triggered by an event determined by the event-processing module 470. The triggering event is associated with a context entry point in the guideline, and the core engine 444 starts processing at that entry point. The core engine 444 determines the steps in the guideline to be executed according to the internal guideline representation generated by the reading module 416. The steps may be implemented sequentially in accordance with an activity graph or a decision map in the guideline or alternatively may be carried out following a temporal transition such as the elapsing of a set period of time. Execution continues until a blocking node for the patient is reached. It should be noted that blocking nodes in each guideline will vary for each patient as execution paths followed in the guideline are dependent on the patient's data profile.

Evaluator Module/Concept Handler

As the core engine 444 traverses nodes in the guideline, it encounters decision nodes that may contain criteria to be evaluated. For example, a decision node may require the evaluation of whether the systolic blood pressure of a patient surpasses a certain level. The evaluator module 456 can perform the evaluation. It obtains the relevant patient data (e.g., the systolic blood pressure) using the remote data access module 480. The returned value from the CIS 150 will contain a numeric value and a unit of measurement. The evaluator module 456 obtains a normal or threshold systolic blood pressure value from the CIS 150 to be compared with the patient's blood pressure, also expressed in terms of an unit of measurement. The evaluator module 456 can perform any unit conversions required for the evaluation and then perform the comparison. To help the core engine 444 process terms included in the guideline, a concept handler module 448 interacts with the terminology server 180 to obtain necessary subsumption and other terminology data. The concept handler 448 may also determine when to use subsumption in the first place. For example, if the guideline asks: "is the patient taking ibuprofen?," the concept handler 448 contains logic directing the core engine 444 to use subsumption information to examine the patient's records in the CIS 150 to determine if the patient is taking any one of the different painkillers that include ibuprofen. In contrast, if the guideline specifies that a patient should receive a specific type of ibuprofen (e.g., Motrin), the concept handler 448 directs the core engine 444 to query the CIS 150 for Motrin, and not for just any type of ibuprofen.

Function Handler

A function handler module 452 assists the core engine 444 in processing portions of guidelines that cannot adequately be expressed in the chosen representational form. The functional handler 452 implements an expressional language that in which arbitrarily complex concepts may be expressed. For instance, certain concepts are difficult to express in the Protégé format; the concept of "if platelet count+20 is >x" cannot be encoded accurately. In one embodiment, the core engine 444 interprets a Protégé guideline up to the point of this concept. At that point, an alternative logic sequence expressing the concept is provided to fill in the gap. The sequence can be hand-coded and expressed in any variety of non-Protégé formats. The function handler 452 processes this and other such "escape sequences."

Scheduling Module

The scheduling module 458 implements temporal constructs used by the guideline execution engine 100. When the core engine 444 encounters a temporal transition (for example, under which a certain action is to take place only after a certain time period, X, has elapsed), it registers the transition with the scheduling module 458, which records the registration in a database stored in the engine 100 for instance. The scheduling module 458 implements an internal clock that monitors the registration in its database. When the scheduled registration time arrives (i.e., at $t_0+X$), the scheduling module 458 activates the event specified during the registration in conjunction with the binding module 450. The scheduling module 458 also includes a scheduler that allows the registration of engine internal events such as "execute this sub-guideline at midnight of every third Sunday of the month".

Other Modules

Besides the deployment module 400, binding module 340, and processing module 440, several other modules are used to support guideline execution. An event-processing module 470 receives messages from the event listener 120 and may also monitor the status of internal schedules or other event triggers. At the appropriate time, the event-processing module 470 activates the processing module 440 to interpret a guideline. Events may be generated from external systems such as the CIS 150, a lab system (not shown), an HL7 based interface engine (not shown) or from within the guideline execution engine 100 through the scheduling module 458.

Guideline Execution

Figure 5:
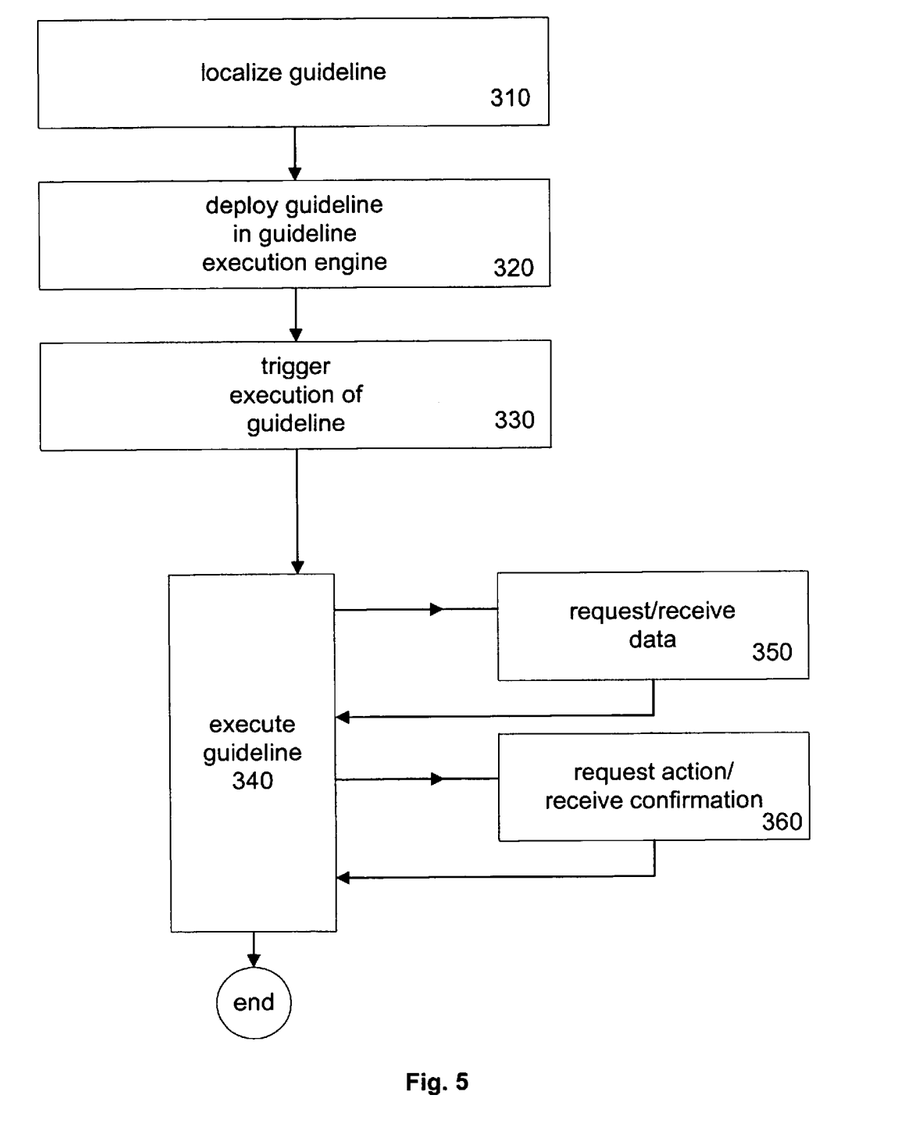
FIG. 5 is a flowchart illustrating the steps of installing and executing a clinical practice guideline by a guideline execution engine in accordance with an embodiment of the invention.

FIG. 5 is a flowchart illustrating a process for installing and interpreting a guideline into the guideline execution engine 100 of FIG. 1 in accordance with an embodiment of the invention. Prior to deployment of the guideline, the guideline may be localized 310 to make it conform to the policies that may be in place at a local clinical organization. The guideline is then deployed 320 in the guideline execution engine 100 by a deployment module 400. A reading module 416 of the deployment module 400 converts the guideline into an interpretable form and determines events of significance that trigger execution of the guideline, and a validation module 408 validates the syntax of the guideline in its new form. Assuming the guideline is valid, an initialization module 412 initializes the guideline, indicating that it is ready to be interpreted. The initialization module 412 calls the binding layer 450, which associates constructs within the guideline with requests for data to be retrieved and actions to be performed during guideline execution.

The initialization module 412 registers triggering events with the event listener 120. In an embodiment, this is a manual process that is done by hand, however, this may also take place through an automated process that occurs, for instance, during deployment of the guideline. Guideline execution may be tested as part of the initialization process, using data stored locally or remotely and accessed through the binding layer 450. Once the guideline has been deployed 320, a "server ready" message is broadcast, setting the stage for guideline execution. Patient enrollment and other aspects of guideline execution and engine 100 management may be administered through a administrative module of the guideline execution engine 100. The CIS 150 or another external system may be used to access the functionality and data available to the engine 100 through an engine access interface 420 of the guideline execution engine 100.

Execution 330 of the guideline may be triggered in any of a variety of ways. In one embodiment, the event listener 120 monitors medical data stored in the CIS 150 to listen for the pre-specified events that will trigger guideline execution. When an event occurs, such as a clerk registering a new patient, the listener 120 sends a notification comprising a "message of interest" to the guideline execution engine 100. Alternatively, a guideline may be triggered by an internal stimulus—based on a schedule for where a guideline is scheduled to run at a certain time, or a time interval if a guideline is set to be interpreted a certain amount of time after an event has occurred, for instance. An event-processing module 470 of the guideline execution engine 100 receives the various event trigger data from external and internal sources and uses it to initiate execution at the appropriate time.

Once execution is triggered, the guideline execution engine 100 executes 340 the guideline for a particular patient. A core engine 444 of the guideline execution engine 100 first performs context processing to determine a starting point for interpretation. As it executes 340 the guideline from this point, the core engine 444 may interact through the concept handler with a terminology server 180 to resolve the meanings of various clinical terms in the guideline. Taking as an example a diabetes guideline, a concept handler 448 can send a "diabetic" term ID to the terminology server 180 to request 350 terminology data, and receive 350 in response a set of all terms subsumed within "diabetic." In a similar way, the core engine 444 may also interact with the function handler 452 to interpret portions of the guideline represented using the expression language implemented in the function handler module 452.

The core engine 444 continues logically processing the nodes of the guideline. Guideline execution 340 may require the core engine 444 to obtain data stored in a CIS 150. A remote data access module 480 of the guideline execution engine 100 requests 350 this information through a binding layer, conforming its requests to methods published by an interface 140. The interface 140 translates the engine 100 requests into CIS-specific calls and obtains the requested data. Under the guideline, the requested information may be compared to a predetermined value or otherwise evaluated by an evaluator 456.

At some point, the engine 100 may reach a decision node in the guideline that for instance requires input from a clinician. An execution module 460 of the engine 100 uses a web services call to send a message (i.e., a notification) to the interface 140, which in turn requests 350 the needed data from the clinician through the CIS 150. Until this information is received 350, the guideline path is in "blocked" mode. Once the query is answered 350, the engine 100 resumes execution of the guideline. Execution of a guideline can be "blocked" in other ways. For instance, execution of an activity graph can be interrupted when execution reaches a context node that requires an external triggering event—until this event occurs that thread of execution is blocked. This may be represented in a guideline as requiring a new session. In addition, blocking can occur if a time interval needs to elapse before a node is executed. When the execution engine 100 detects that the time has passed, it sends an internal event notification to the event processing module 470. The core engine 444 may release the blocked node and continue execution. The thread of execution may also be blocked at some nodes that may require multiple predecessor nodes to complete their execution before execution of the particular node can begin. It should be noted, however, that notwithstanding the occurrence of "blocked nodes," several guideline portions can execute concurrently, and several paths within an activity graph or decision map may execute concurrently, resulting in multiple active or blocked threads of guideline execution for a patient at a given point in time.

At a certain stage, the engine 100 may also reach a node in the guideline that requires an action to be taken such as the scheduling of an appointment. The guideline execution engine 100 requests 360 that this action be executed on the CIS 150, again through the interface 140, and receives 360 a confirmation or data in return. At some point during execution, an action node is presented in accordance with the guideline, for instance instructing the immunization of a patient. The remote data access module 480 of the engine 100 calls the actions module 520 of the interface 140 and requests 360 an action or actions associated with the action node (e.g., order vaccine, schedule immunization). The interface 140 carries out this request 360, for instance, on the order module 560a and appointments module 560d of the CIS 510. The interface 140 could also generate and deliver a notification to the clinician through the notifications module 560c informing her of the presence of the vaccine order waiting to be approved. Confirmation that the order has been prepared and later, that the clinician has approved the request, are returned 360 to the engine 100. Execution of the guideline 340 continues until the paths of execution are exhausted, some blocking event such as "response expected from a clinician" occurs, a context node requires a new triggering event to continue, the patient withdraws from the CIS or other terminating event.

While the foregoing describes the invention in connection with preferred embodiments thereof, it will be understood that it is not intended to limit the invention to those embodiments. On the contrary, it does not cover all alternatives, modifications, and equivalents as may be included within the spirit and scope of the invention as defined by the claims.

We claim:

1. A guideline execution system including an automated guideline execution engine for executing a clinical practice guideline (CPG) based on patient medical data stored in a clinical information system (CIS), the system comprising:
 a storage device coupled to a bus, the storage device including a set of executable code; and
 a processor coupled to the bus, wherein the processor executes the set of executable code, effectuating the following elements:
  a core engine configured in the guideline execution engine, wherein the core engine executes the CPG, wherein the CPG is a standardized clinical practice workflow for a medical procedure or practice;
  a binding module configured in the guideline execution engine, wherein the binding module obtains medical data stored in the CIS responsive to execution of the CPG, and further implements an action responsive to execution of the CPG based on the medical data obtained from the CIS, wherein the binding module includes a remote data access module and a local data access module, further wherein the local data access module provides or overrides clinical functionality in the CIS;
  an actions interface coupling the guideline execution engine and the CIS, wherein the actions interface receives and transfers requests from the guideline execution engine to the CIS during the execution of the CPG and receives and transfers responses from the CIS to the guideline execution engine, wherein the actions interface communicates with the guideline execution engine in a first protocol and the CIS in a second protocol, wherein the remote data access module in the binding module formulates the request to the action interface and forwards responses to the core engine;
  an event listener, wherein the event listener monitors changes in and additions to medical data stored in the CIS for a triggering event, and further wherein the event listener sends an event notification of the triggering event to the guideline execution engine; and
  an event processing module in the guideline execution engine, wherein the even processing module receives the event notification and activates the core engine to execute the CPG responsive to the event notification.

2. The system of claim 1, comprising a concept handler, wherein the concept handler obtains terminology data for a term included in the clinical practice guideline from a terminology server and returns the terminology data to the core engine for execution of the term.

3. The system of claim 1, comprising a function handler, wherein the function handler process apportions the guideline not intended for execution by the core engine and returning a result based on the processing to the core engine.

4. The system of claim 1, comprising a reading module, wherein the reading module parses the guideline and determining triggering events based on the guideline.

5. The system of claim 1, wherein the binding module receives requests for medical data from the core engine, retrieves requested medical data through an interface layer form a plurality of sources, and provides retrieved requested medical data to the core engine to support execution of the guideline.

6. The system of claim 5, wherein the binding module creates a request for the medical data formatted according to a web services protocol supported by the interface layer.

7. The system of claim 1, wherein the binding module generates a request to perform an action in the CIS formatted according to a web services protocol published by an interface layer between the engine and the CIS.

* * * * *